(12) United States Patent
Watanabe

(10) Patent No.: US 8,401,150 B2
(45) Date of Patent: Mar. 19, 2013

(54) RADIATION IMAGING SYSTEM AND RELAY STATION SELECTION METHOD

(75) Inventor: Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 211 days.

(21) Appl. No.: 12/912,048

(22) Filed: Oct. 26, 2010

(65) Prior Publication Data

US 2011/0108732 A1    May 12, 2011

(30) Foreign Application Priority Data

Nov. 9, 2009    (JP) ................. 2009-256546

(51) Int. Cl.
*H05G 1/58* (2006.01)
(52) U.S. Cl. .................... 378/114; 378/98.8
(58) Field of Classification Search .......... 378/62, 378/98.8, 114–116; 250/370.08, 370.09
See application file for complete search history.

(56) References Cited

U.S. PATENT DOCUMENTS

| 2009/0154648 A1 | 6/2009 | Watanabe | 378/116 |
| 2010/0054404 A1 | 3/2010 | Watanabe | 378/62 |

FOREIGN PATENT DOCUMENTS

| JP | 08-116044 | 5/1996 |
| JP | 2003-210444 | 7/2003 |

*Primary Examiner* — Courtney Thomas
(74) *Attorney, Agent, or Firm* — Fitzpatrick, Cella, Harper & Scinto

(57) ABSTRACT

This invention includes a radiation detector to detect the radiation transmitted through an object while being in a portable state or mounted on a detector holder, a control unit to control capturing of a radiographic image using the radiation detector, and a plurality of relay stations to relay wireless communication from the radiation detector. The detector holder includes a detection unit to detect the mounting of the radiation detector. The control unit determines the usage pattern of the radiation detector or the mounting of the radiation detector on a detector holder based on detection information from the detection unit or a connection request from the radiation detector, and selects one of the relay stations based on the determination result.

41 Claims, 7 Drawing Sheets

RADIATION IMAGING SYSTEM AND RELAY STATION SELECTION METHOD

BACKGROUND OF THE INVENTION

1. Field of the Invention

The present invention relates to a radiation imaging system and a relay station selection method.

2. Description of the Related Art

There is known a radiation imaging system which captures a radiographic image of an object by irradiating an object with radiation (for example, X-rays) and detecting the intensity distribution of the radiation transmitted through the object. Such a system is widely used in the medical and industrial fields and the like.

Such radiography sometimes uses a semiconductor sensor like that disclosed in Japanese Patent Laid-Open No. 8-116044. Radiography using a semiconductor sensor can obtain a very wide dynamic range as compared with conventional radiography using photosensitive films, and hence can obtain radiographic images which are free from the influences of variations in the radiation dose upon exposure. In addition, unlike the conventional photosensitive film scheme, this technique need not perform any chemical process and can instantly obtain an output image. An imaging system using a semiconductor sensor is mainly divided into a radiation imaging unit to acquire images and a control unit to control the image acquisition of the imaging unit and display captured images on a monitor.

Recently, a flat, lightweight, portable imaging unit (also called an electronic cassette) has been required to allow quicker radiography of regions in a wider range. A high-speed communication cable has been used between the imaging unit and the control unit to implement real-time image display. Such a cable, however, becomes an obstacle when the operator moves the portable imaging unit or installs the imaging unit in a desired position. This degrades the operability. For the sake of an improvement in communication performance by wireless as well, a wireless electronic cassette like that disclosed in Japanese Patent Laid-Open No. 2003-210444 has also been proposed.

There are various types of detector holders to position an electronic cassette to a subject in accordance with a desired imaging form. Such detector holders include a stand for chest radiography to be performed in a standing position and an imaging table in a decubitus state. Each detector holder includes a housing unit to mount an electronic cassette. The housing unit holds the electronic cassette so as to properly position it with respect to a radiation generator.

In general, a housing unit is often formed from a metal housing which contains an electronic cassette. The metal housing becomes a factor that degrades wireless communication performance between a wireless antenna built in the electronic cassette and an external wireless communication unit connected to the control unit.

In addition, such an external wireless communication unit is generally provided singly. That is, such a system has not been configured to perform wireless communication between the electronic cassette and the control unit upon selecting one of a plurality of wireless communication units.

SUMMARY OF THE INVENTION

The present invention provides a technique of determining the usage pattern of an electronic cassette (radiation detector) or the detector holder on which the electronic cassette is mounted and selecting one of a plurality of relay stations based on the determination result.

According to a first aspect of the present invention there is provided a radiation imaging system comprising: a radiation detector configured to detect radiation transmitted through an object while being in one of a portable state and a mounted state on a detector holder; a control unit configured to control capturing of a radiographic image using the radiation detector; and a plurality of relay stations configured to relay wireless communication from the radiation detector, the detector holder comprising a detection unit configured to detect mounting of the radiation detector, and the control unit comprising: a determination unit configured to determine one of a usage pattern of the radiation detector and mounting of the radiation detector on a detector holder based on one of detection information from the detection unit and a connection request from the radiation detector, and a selection unit configured to select one of the relay stations based on a determination result by the determination unit.

According to a second aspect of the present invention there is provided a control apparatus which controls capturing of a radiographic image using a radiation detector configured to detect radiation transmitted through an object while being in a portable state or mounted on a detector holder, the apparatus comprising: a determination unit configured to determine one of a usage pattern of the radiation detector and mounting of the radiation detector on a detector holder based on one of information from the detector holder and a connection request from the radiation detector; and a selection unit configured to select a relay station, from a plurality of relay stations, which relays wireless communication from the radiation detector, based on a determination result by the determination unit.

According to a third aspect of the present invention there is provided a radiation detector which detects radiation transmitted through an object while being in one of a portable state and a mounted state on a detector holder, the detector comprising: a determination unit configured to determine one of a usage pattern of the radiation detector and mounting of the radiation detector on a detector holder; and a selection unit configured to select one of the relay stations based on a determination result by the determination unit.

According to a fourth aspect of the present invention there is provided a relay station selection method in a radiation imaging system comprising a radiation detector configured to detect radiation transmitted through an object while being in one of a portable state and a mounted state on a detector holder, a control unit configured to control capturing of a radiographic image using the radiation detector, and a plurality of relay stations configured to relay wireless communication from the radiation detector, the method comprising: determining one of a usage pattern of the radiation detector and mounting of the radiation detector on a detector holder based on one of detection information indicating mounting of the radiation detector and a connection request from the radiation detector; and selecting one of the relay stations based on the determination result.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

Although the following embodiments will exemplify a case in which X-rays are used as radiation, radiation to be used may be electromagnetic waves, α rays, β rays, γ rays, and the like.

First Embodiment

Figure 1:
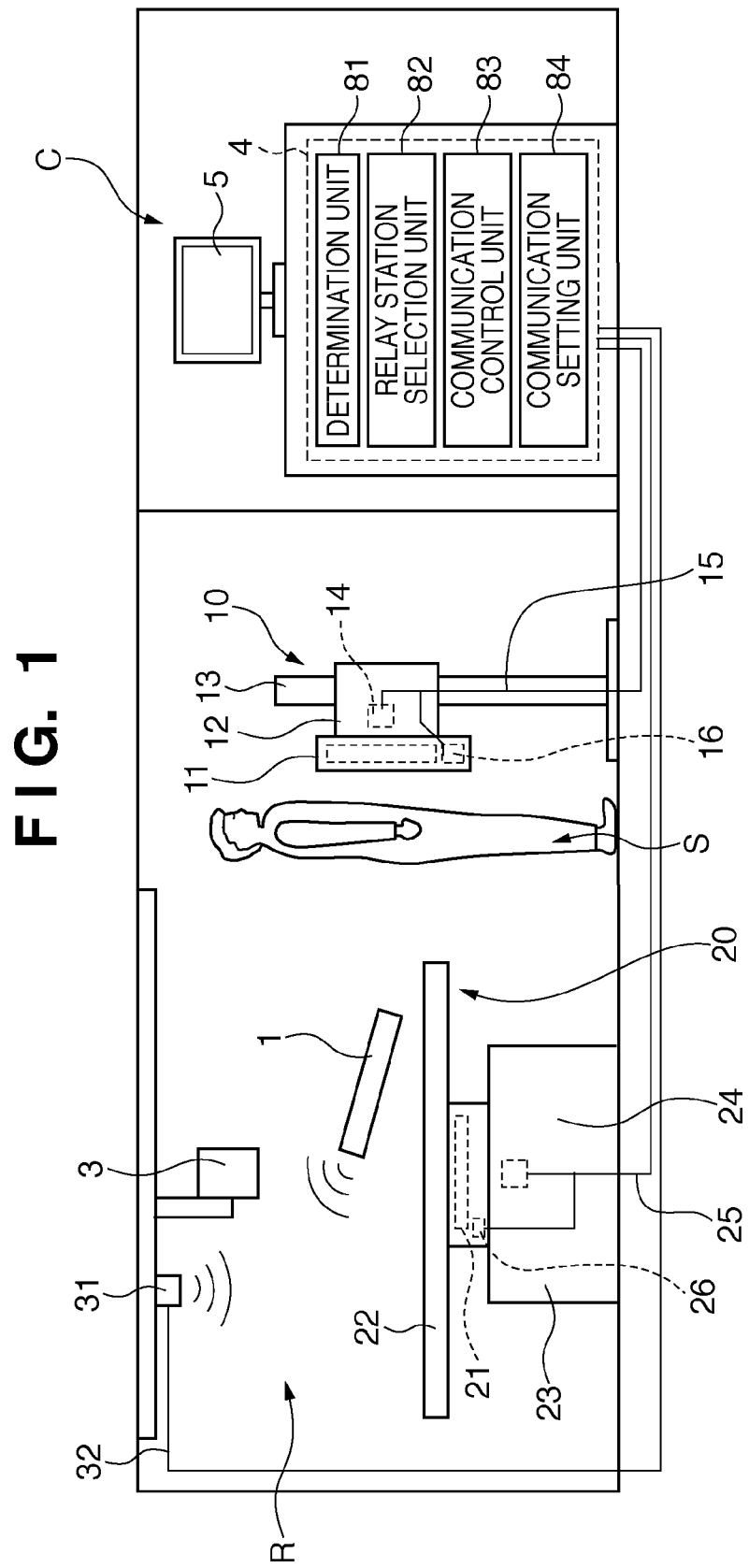
FIG. 1 is a view showing the schematic arrangement of a radiation imaging system according to an embodiment of the present invention.

FIG. 1 is a view showing an example of the schematic arrangement of a radiation imaging system (to be referred to as an X-ray imaging system hereafter) according to an embodiment of the present invention.

In general, facilities for X-ray imaging are divided into an imaging room R and an operation room C to separate radiation management zones. In the imaging room R, X-ray imaging is performed. In the operation room C, the operator performs imaging operation and image checking operation. For this reason, an electronic cassette 1 and an X-ray generator 3 are provided in the imaging room R. A control unit (control apparatus) 4 and a monitor 5 are provided in the operation room C. Wireless relay stations 14, 24, and 31 are installed in the imaging room R to implement wireless communication between the electronic cassette 1 in the imaging room R and the control unit 4. The wireless relay stations 14, 24, and 31 perform wireless communication with the electronic cassette 1 in accordance with preset wireless specifications.

In this case, the X-ray generator 3 functions as a radiation generator. More specifically, the X-ray generator 3 includes an X-ray tube and applies X-rays to an object (that is, a subject).

Figure 2:
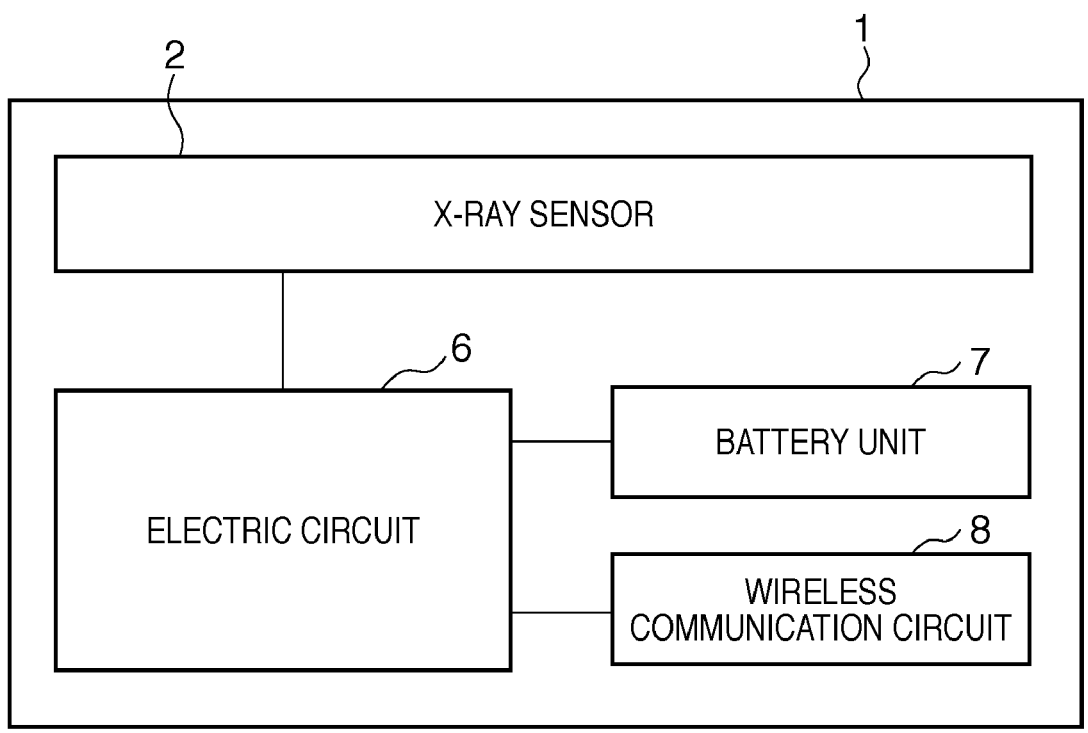
FIG. 2 is a block diagram showing an example of the arrangement of an electronic cassette 1 shown in FIG. 1.

The electronic cassette (to be sometimes abbreviated as a cassette) 1 functions as a radiation detector which detects the X-rays transmitted through an object and acquires an X-ray image (radiographic image) based on the object. As shown in FIG. 2, the electronic cassette 1 incorporates an X-ray sensor 2. For example, photo-electric conversion elements arrayed in a two-dimensional lattice pattern detect the X-rays transmitted through the object. In addition to the X-ray sensor 2, the electronic cassette 1 incorporates an electric circuit 6, a battery unit 7, a wireless communication circuit 8, and the like. The electric circuit 6 controls imaging operation such as driving of the X-ray sensor 2 and read operation, and communicates with the control unit 4. The battery unit 7 supplies power to the respective units of the electronic cassette 1. The wireless communication circuit 8 includes an antenna and exchanges control and image signals with the control unit 4.

In this case, the control unit 4 includes one or a plurality of computers. A computer includes, for example, a main control unit such as a CPU and storage units such as a ROM (Read Only Memory) and a RAM (Random Access Memory). The computer may also include a communication unit such as a network card and input/output units such as a keyboard, a display, and a touch panel. Note that these constituent elements are connected via a bus and the like. The main control unit controls them by reading out and executing programs stored in the storage units.

The control unit 4 comprehensively controls processing in the X-ray imaging system. The control unit 4 controls, for example, imaging operation by the electronic cassette 1 and causes the monitor 5 to display the image captured by the electronic cassette 1.

In this case, when an X-ray image is to be captured, it is necessary to adjust the positional relationship between the electronic cassette 1 and the subject. This positional relationship is adjusted in accordance with a region to be radiographed and the state of the subject. Various types of detector holders are used to constantly maintain the state in which the electronic cassette 1 is positioned to the subject.

The electronic cassette 1 is used while being mounted on a detector holder such as a stand (standing-position holder) 10 or an imaging table (decubitus table) 20, or is singly used in a portable state (used in a portable state in the case shown in FIG. 1). When the operator mounts the electronic cassette 1 on the stand 10 or the imaging table 20, the system performs X-ray imaging while holding the posture of the electronic cassette 1 in each state. When, for example, the operator mounts the electronic cassette 1 on the stand 10, the system radiographs a chest region or the like in a standing position (standing-position radiography). When, for example, the operator mounts the electronic cassette 1 on the imaging table 20, the system radiographs a chest region, an abdominal region, or the like in a decubitus position (lying position) (decubitus radiography). These detector holders respectively include housing units 11 and 21 to detachably house the electronic cassette 1 so as to accurately position the electronic cassette 1 to the X-ray generator 3.

The housing units 11 and 21 each have a housing structure to contain the electronic cassette 1, and has an open surface which X-rays strike. The housing units 11 and 21 each are formed from a member having high X-ray transmittance. The housing itself is formed by using, for example, a high-strength steel material to make it difficult for X-rays to leak to the rear side in the X-ray incident direction.

Since the electronic cassette 1 is contained in the housing formed from such a steel material (that is, a metal housing), the wireless channel of the antenna built in the electronic cassette 1 is narrowed. The X-ray sensor 2 and the structure which mechanically contains the sensor are positioned on the X-ray incident side which is electromagnetically open. In addition, a grid to remove scattered radiation, photo timer to control the dose of X-rays, and the like (none of which are shown) are arranged on the X-ray incident side. This is also a factor that narrows the wireless channel. Therefore, housing the electronic cassette 1 in the housing 11 or 21 will degrade the wireless transfer performance. For this reason, this embodiment includes wireless relay stations in both the interior of the detector holder (the same space as that in the housing of the housing unit 11 or 21) and outside the detector holder.

The stand 10 includes a seat unit 12 which can vertically move relative to a support 13. The housing unit 11 containing the electronic cassette 1 is mounted on the seat unit 12. The seat unit 12 has a space inside, which communicates with the interior of the housing unit 11. The wireless relay station 14 is placed in this space. The wireless relay station 14 is connected to the control unit 4 inside the operation room C via a cable 15.

The imaging table 20 includes a top plate 22 on which a subject S is placed and a detector holder unit 23 which supports the top plate 22. The housing unit 21 to hold the electronic cassette 1 is provided between the upper portion of the detector holder unit 23 and the lower portion of the top plate 22. The wireless relay station 24 is placed on the lower side in the housing unit 21. The wireless relay station 24 is connected to the control unit 4 in the operation room C via a cable 25.

The electronic cassette 1 is used in a portable state on the top plate 22 of the imaging table 20. In this case, the electronic cassette 1 (wireless communication circuit 8) communicates with the wireless relay station 31 outside the detector holder, which is placed on the ceiling inside the imaging room R. The wireless relay station 31 is connected to the control unit 4 in the operation room C via a cable 32. Communication settings such as wireless channel information and address information are registered in the electronic cassette 1 in advance. The electronic cassette 1 performs communication based on these communication settings. Each relay station performs communication based on the communication settings.

The respective detector holders (the stand 10 and the imaging table 20) are respectively provided with mounting detection units 16 and 26 to detect the mounting of the electronic cassette 1. The mounting detection units 16 and 26 are connected to the control unit 4 to notify the control unit 4 of the detection information. The control unit 4 includes, as functional units, a determination unit 81, a relay station selection unit 82, a communication control unit 83, and a communication setting unit 84. Note that the communication setting unit 84 will not be mentioned in the first embodiment, but will be described in the second and third embodiments.

The determination unit 81 determines the usage pattern of the electronic cassette 1 or on which one of the detector holders the electronic cassette 1 is mounted. The determination unit 81 performs this determination based on the detection information received from the detector holder or the connection request received from the electronic cassette 1 via one of the relay stations. The relay station selection unit 82 selects one of the wireless relay stations based on the determination result. The communication control unit 83 controls communication with the electronic cassette 1 via the selected relay station. With this operation, the control unit 4 automatically switches the wireless relay stations to perform communication. Note that the determination unit 81 may determine from which detector holder detection information has received, by, for example, assigning pieces of detection information from a plurality of detector holders to the respective bits. Upon receiving a connection request without receiving any detection information indicating the detection of the mounting of a detector holder, the determination unit 81 determines that the electronic cassette 1 is used on the top plate 22 of the imaging table 20 in a portable state. In this case, the relay station selection unit 82 selects the wireless relay station 31 placed on the ceiling.

An example of the operation of the control unit 4 shown in FIG. 1 will be described next with reference to FIG. 3. The operation to be performed when X-ray imaging is performed will be described below.

When capturing an X-ray image, the operator acquires an imaging order from information from an RIS (Radiology Information Systems) or the like, and mounts the electronic cassette 1 on the corresponding detector holder in accordance with the corresponding imaging technique. One of the mounting detection units 16 and 26 then detects the mounting of the electronic cassette 1 on the detector holder, and sends corresponding detection information to the control unit 4.

Upon receiving the detection information, the control unit 4 causes the determination unit 81 to determine the detector holder on which the electronic cassette 1 is mounted (YES in step S101). The determination result indicates that the electronic cassette 1 is mounted on the stand 10 ("stand" in step S103), the control unit 4 causes the relay station selection unit 82 to select the wireless relay station 14 provided in the stand 10 (S104). If the detector holder on which the electronic cassette 1 is mounted is the imaging table 20 ("imaging table" in step S103), the control unit 4 causes the relay station selection unit 82 to select the wireless relay station 24 provided in the imaging table 20 (S105).

Upon receiving a connection request without receiving any detection information (YES in step S102 after NO in step S101), the control unit 4 causes the determination unit 81 to determine that the electronic cassette 1 is used in a portable state. In this case, the control unit 4 causes the relay station selection unit 82 to select the wireless relay station 31 to be used when the electronic cassette is used in a portable state (outside the detector holders) (S106). Upon selecting a relay station in this manner, the control unit 4 starts to communicate with the electronic cassette 1 via the selected relay station (S107).

As described above, the first embodiment is configured to determine the usage pattern of the electronic cassette 1 or the detector holder on which the electronic cassette 1 is mounted and perform communication upon selecting one of a plurality of relay stations in accordance with the determination result. This improves the quality of wireless communication between the electronic cassette 1 and the control unit 4. For example, this makes it possible to secure a stable wireless communication channel even while the electronic cassette 1 is mounted on a detector holder. Note that since only one wireless relay station operates at the same time, no interference occurs in wireless communication.

Second Embodiment

The second embodiment will be described next. The second embodiment will exemplify a case in which a plurality of electronic cassettes 1 are provided.

Figure 4:
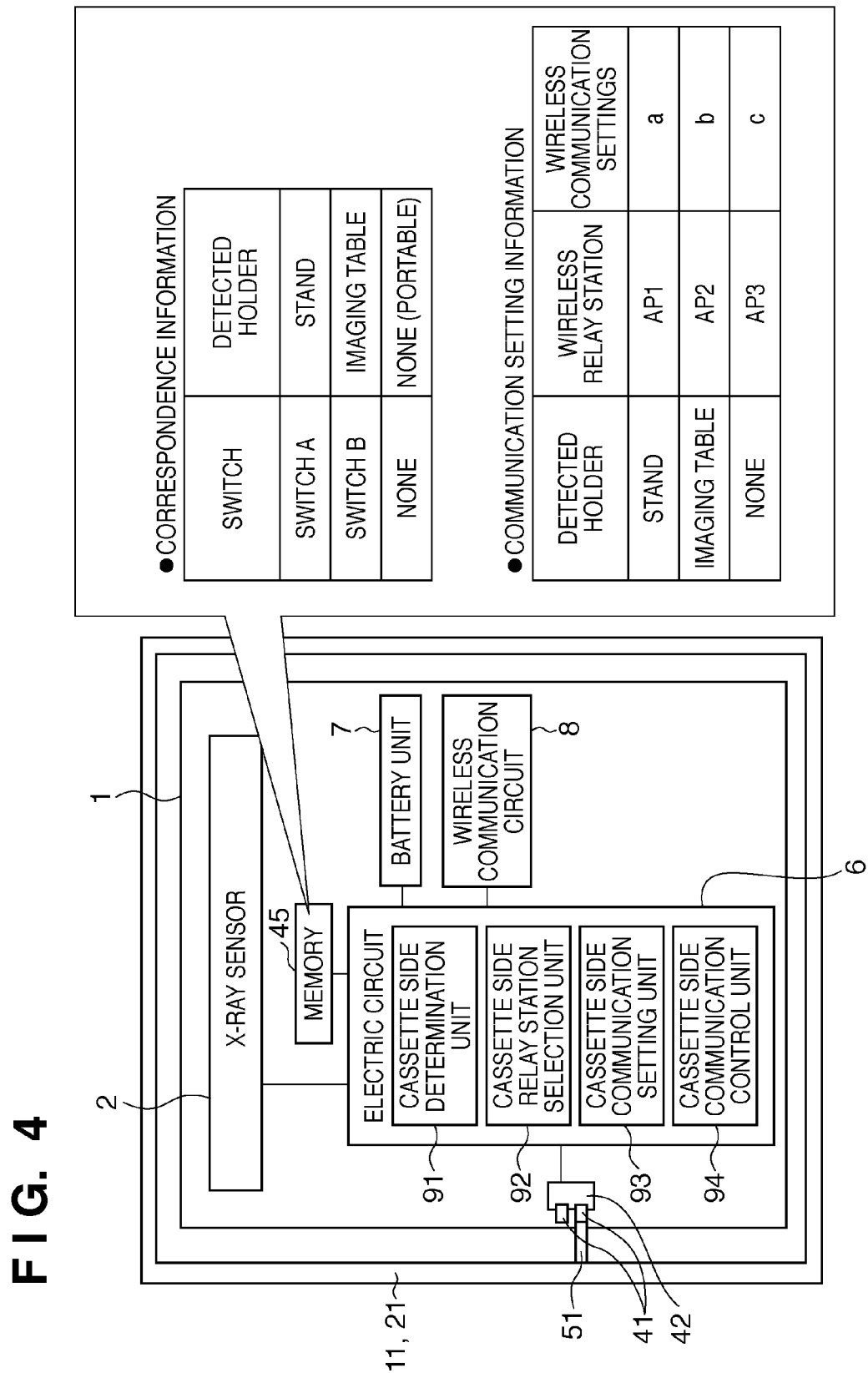
FIG. 4 is a block diagram showing an example of the arrangement of an electronic cassette 1 according to the second embodiment.

FIG. 4 is a block diagram showing an example of the arrangement of an electronic cassette 1 according to the second embodiment.

The electronic cassette 1 is provided with a detector holder mounting detection unit 42 including a plurality of switches 41 (two in this case). A protrusion 51 is formed on the interior of each of housing units 11 and 21 of a stand 10 and imaging table 20. The protrusion 51 is placed at a position where it can press the switch 41. The protrusions 51 differ in shape for the respective housing units. For this reason, the different switches 41 of the electronic cassette 1 are pressed depending on the housing units 11 and 21. This allows the electronic cassette 1 to detect, based on the pressed state of one of the switches 41, the detector holder on which the electronic cassette is mounted. Note that the control unit 4 can detect, based on detection information from a mounting detection unit 16 or 26 provided on the detector holder side, the detector holder on which the electronic cassette 1 has been mounted.

The electronic cassette 1 includes a memory 45 in addition to the arrangement shown in FIG. 2 described in the first embodiment. The memory 45 functions as a radiation detector side storage unit to store various kinds of information, and stores correspondence information and communication setting information. The correspondence information to be stored includes information associating the switches 41 with the detector holders and the like.

The communication setting information to be stored includes a wireless relay station optimal for each usage pattern of the electronic cassette 1 and communication settings (for example, information such as a frame rate) unique to each wireless relay station. Both the electronic cassette 1 and the control unit 4 hold this information. According to the communication setting information shown in FIG. 4, for example, upon detecting that the electronic cassette 1 is mounted on the stand 10, the electronic cassette 1 selects AP1 as a wireless relay station and performs communication in accordance with wireless communication settings a. Upon detecting that the electronic cassette 1 is mounted on the imaging table 20, the electronic cassette 1 selects AP2 as a wireless relay station and performs communication in accordance with wireless communication settings b. Upon detecting that the electronic cassette 1 is not mounted on any detector holder, the electronic cassette 1 selects AP3 as a wireless relay station and performs communication in accordance with wireless communication settings c.

It is possible to set these pieces of information by using software on the control unit 4 side. For example, the control unit 4 may provide setting information to the electronic cassette 1 via another communication tool such as a cable. This can prevent erroneous settings in a plurality of combinations of the control unit 4 and the electronic cassette 1.

An electric circuit 6 of the electronic cassette 1 includes, as functional units, a cassette side determination unit 91, a cassette side relay station selection unit 92, a cassette side communication setting unit 93, and a cassette side communication control unit 94. The cassette side determination unit 91 functions as a radiation detector side determination unit and determines the usage pattern of the electronic cassette 1 or one of the detector holders on which the electronic cassette 1 is mounted. The cassette side determination unit 91 performs this determination by referring to the above correspondence information using press state information from the switch 41 and information (the start of connection processing and the like) associated with the communicating operation of a wireless communication circuit 8.

The cassette side relay station selection unit 92 functions as a radiation detector side relay station selection unit and selects one of the wireless relay stations based on the determination result obtained by the cassette side determination unit 91. The cassette side communication setting unit 93 functions as a radiation detector side communication setting unit and performs communication setting (setting a relay station, a frame rate, and the like) based on the determination result obtained by the cassette side determination unit 91. This setting includes the above communication setting information. The cassette side communication control unit 94 functions as a radiation detector side communication control unit and executes communication in accordance with the communication settings set by the cassette side communication setting unit 93 via the relay station selected by the cassette side relay station selection unit 92.

The control unit 4 also includes a communication setting unit 84. The communication setting unit 84 provided for the control unit 4 executes a function similar to that of the cassette side communication setting unit 93 provided for the electronic cassette 1, and hence a detailed description of them will be omitted.

Figure 5:
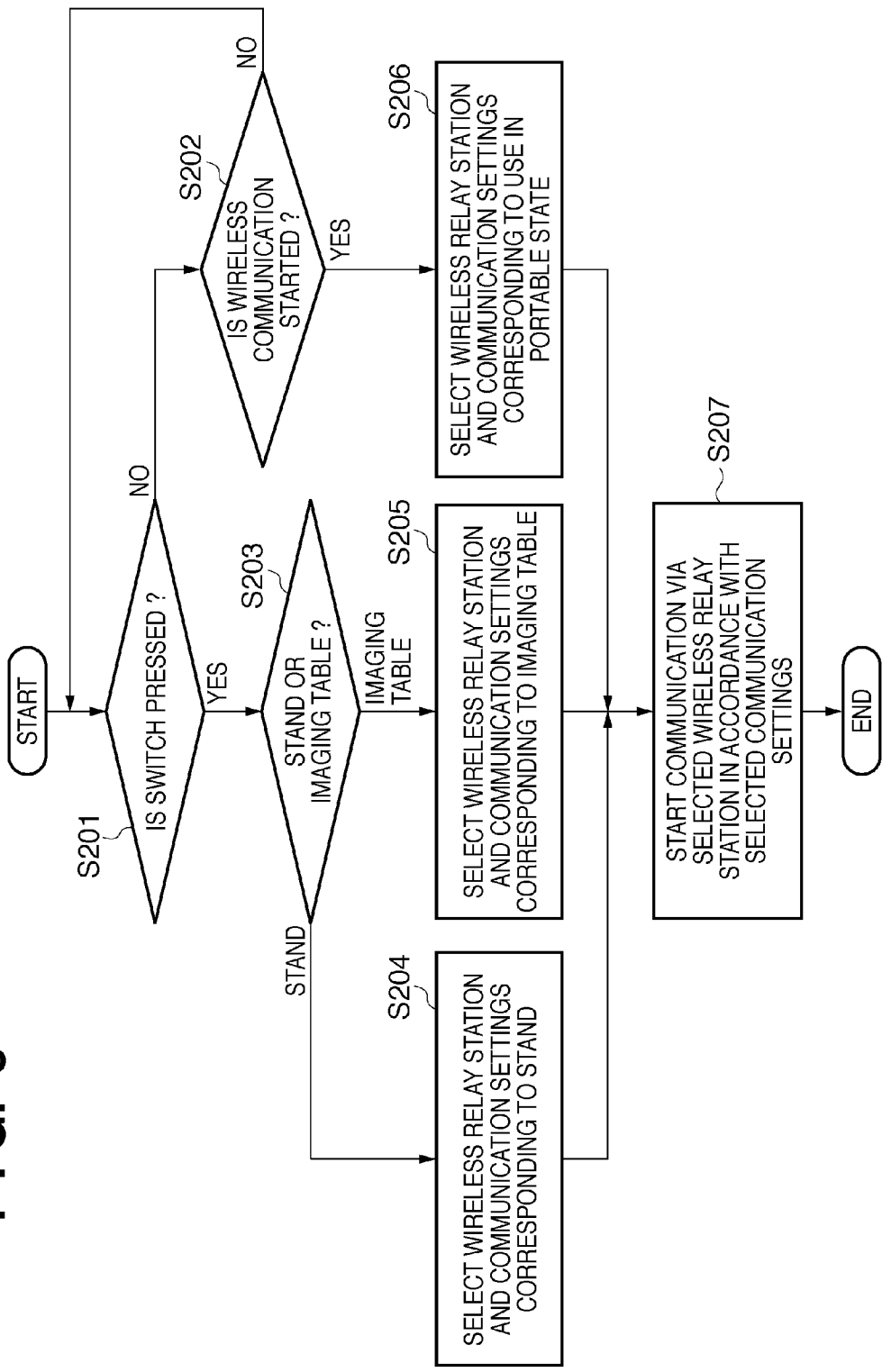
FIG. 5 is a flowchart showing an example of the operation of the electronic cassette 1 according to the second embodiment.

An example of the operation of the electronic cassette 1 according to the second embodiment will be described next with reference to FIG. 5. Operation to be performed when X-ray imaging is performed will be described below.

When capturing an X-ray image, the operator acquires an imaging order from information from an RIS (Radiology Information Systems) and the like, and mounts the electronic cassette 1 on the corresponding detector holder to suit the imaging technique. The protrusion 51 provided on the detector holder then presses the switch 41 provided on the electronic cassette 1.

In this case, the electronic cassette 1 causes the cassette side determination unit 91 to determine the detector holder on which the electronic cassette 1 is mounted, based on which switch 41 is pressed (S201). If the determination result indicates that the detector holder on which the electronic cassette 1 has been mounted is the stand 10 ("stand" in step S203), the electronic cassette 1 causes the cassette side relay station selection unit 92 to select the wireless relay station AP1 corresponding to the stand 10. At this time, the electronic cassette 1 also causes the cassette side communication setting unit 93 to select the communication settings a corresponding to the stand 10 (S204).

If the detector holder on which the electronic cassette has been mounted is the imaging table 20 ("imaging table" in step S203), the electronic cassette 1 causes the cassette side relay station selection unit 92 to select the wireless relation station AP2 and communication settings corresponding to the imaging table 20. At this time, the electronic cassette 1 also causes the cassette side communication setting unit 93 to select the communication settings b corresponding to the imaging table 20 (S205).

Upon receiving a notification of the start of wireless communication from the wireless communication circuit 8 while no switch 41 is pressed (YES in step S202 after NO in step S201), the electronic cassette 1 causes the cassette side relay station selection unit 92 to select the wireless relay station AP3 corresponding to the use of the electronic cassette in a portable state. At this time, the electronic cassette 1 causes the cassette side communication setting unit 93 to select the communication settings c corresponding to the use of the electronic cassette in a portable state (S206). Note that the notification of the start of wireless communication is a notification triggered by transmitting operation by the user or the start or end of X-ray imaging.

Upon selecting a relay station and communication settings in this manner, the electronic cassette 1 causes the cassette side communication control unit 94 to start communication with the control unit 4 based on the selected communication settings via the selected relay station (S207).

Figure 3:
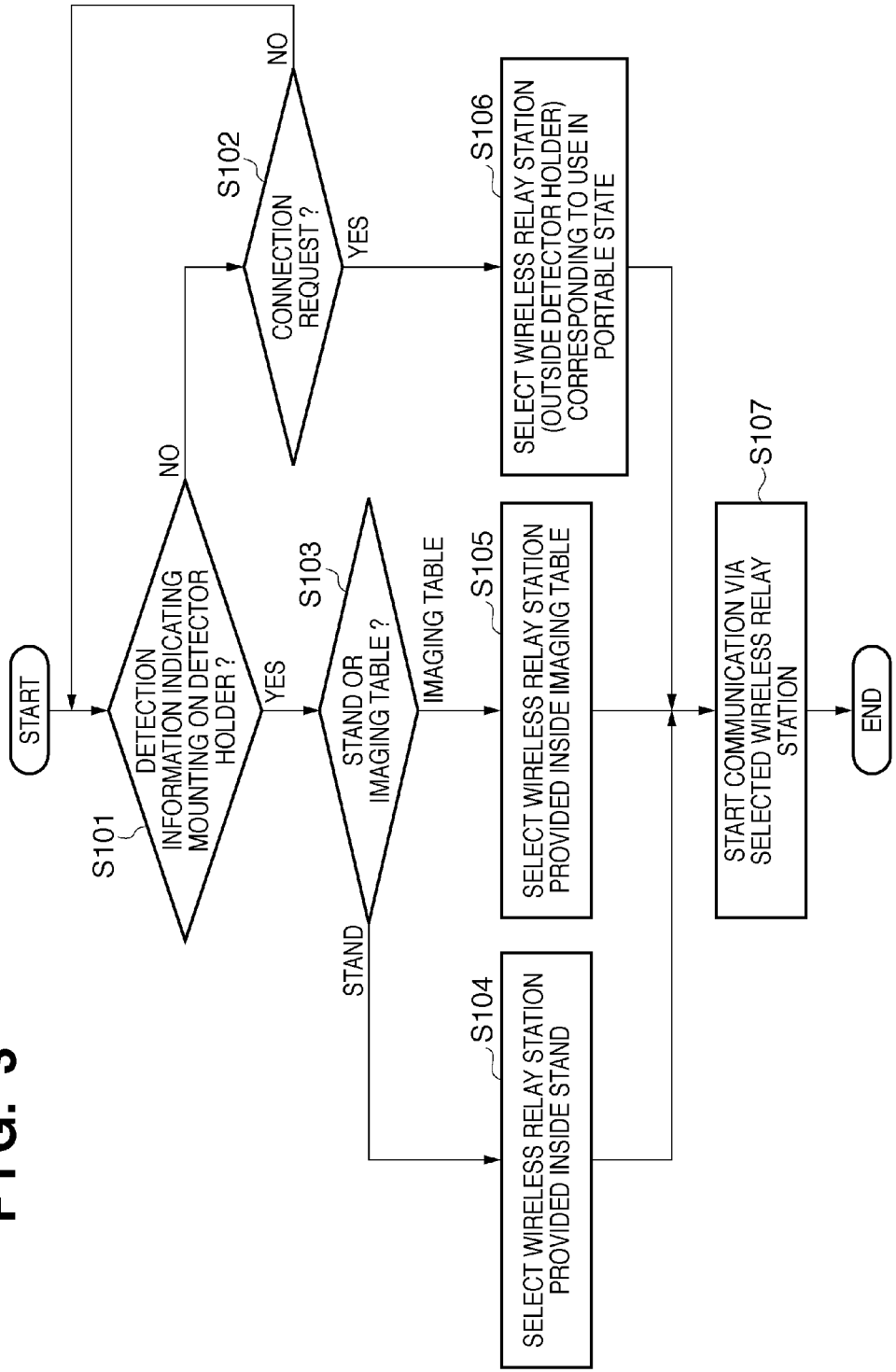
FIG. 3 is a flowchart showing an example of the operation of a control unit 4 shown in FIG. 1.

Note that the operation of the control unit 4 is similar to that shown in FIG. 3, which explains the first embodiment, and hence a description using FIG. 3 will be omitted. A difference between them is that when a relay station is selected, communication setting is performed in the same manner as the electronic cassette 1 described above. As described above, the control unit 4 stores communication setting information with the same contents as those on the electronic cassette 1 side (for example, a ROM or the like may be used as a storage unit).

As described above, the second embodiment is configured to determine, on the electronic cassette 1 side, the usage pattern of the electronic cassette or the detector holder on which the electronic cassette is mounted, and to decide a relay station and communication settings in accordance with the determination result. The electronic cassette 1 then performs communication based on the decided communication settings via the decided relay station. That is, the electronic cassette 1 discriminates wireless communication settings for each imaging form. This implements stable communication and prevents interference when a plurality of electronic cassettes 1 are provided.

Third Embodiment

The third embodiment will be described next. In the first and second embodiments described above, a wireless relay station is provided in each detector holder, and each wireless relay station and the electronic cassette 1 are associated one-to-one with each other. The third embodiment will exemplify a case in which such association is not made.

Figure 6:
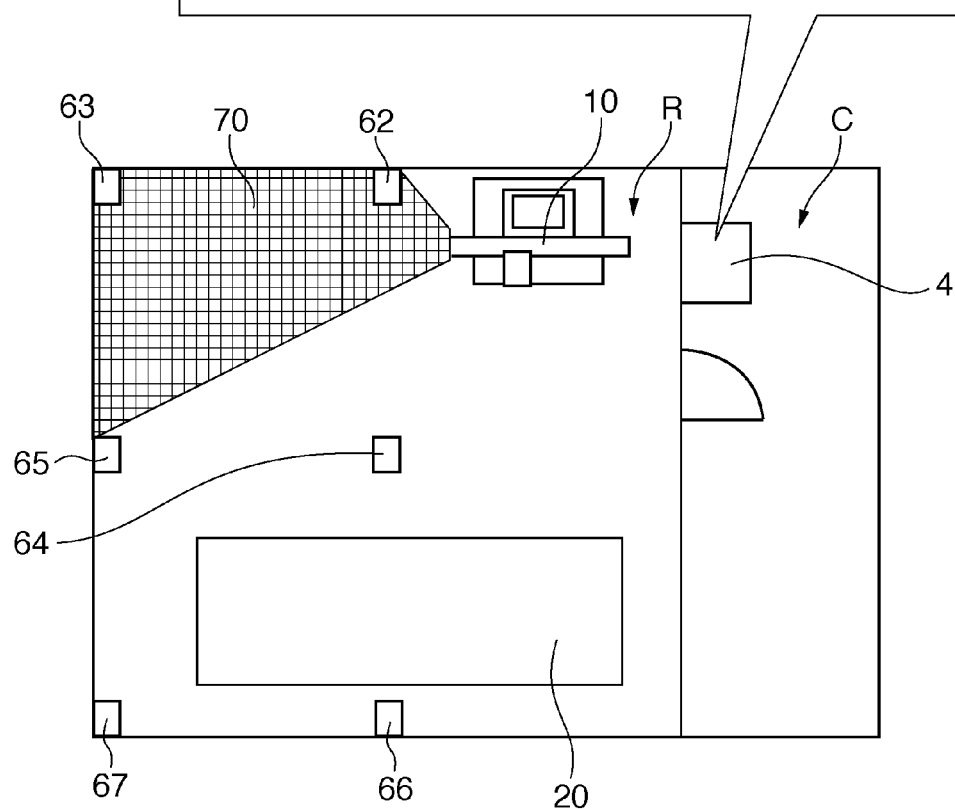
FIG. 6 is a view showing an example of the schematic arrangement of a radiation imaging system according to the third embodiment.

FIG. 6 is a view showing an example of the schematic arrangement of a radiation imaging system according to the third embodiment. FIG. 6 is an overhead view of the imaging room R and operation room C shown in FIG. 1, with reference to which the first embodiment has been described.

In this case, when mounting an electronic cassette 1 in a housing unit 11 or 21, the operator often laterally inserts and removes the cassette in and from the housing unit. Therefore, providing a wireless communication channel in this direction will facilitate securing the wireless communication performance. In this case, however, it is difficult to maintain the wireless communication performance for all the housing units 11 and 21 (detector holders) by using one wireless relay station.

In the third embodiment, a plurality of wireless relation stations 62 to 67 are arranged in the imaging room R. In this case, when selecting a relay station, a relay station selection unit 82 of a control unit 4 according to the third embodiment refers to communication setting information. The relay station selection unit 82 then selects relay station candidates based on this reference, and scans the communication levels (communication intensities) between the relay station candidates and the electronic cassette 1. With this operation, the relay station selection unit 82 determines the communication level of each relay station at this time point, and selects a wireless relay station exhibiting the optimal performance. This operation can perform communication setting more quickly than scanning all the wireless relay stations. In this case, if, for example, the electronic cassette 1 is mounted in a stand 10, communication is performed from the mounting port on the lateral side. In this case, the relay station selection unit 82 selects a wireless relay station located in a region 70 as a relay station to be used.

Figure 7:
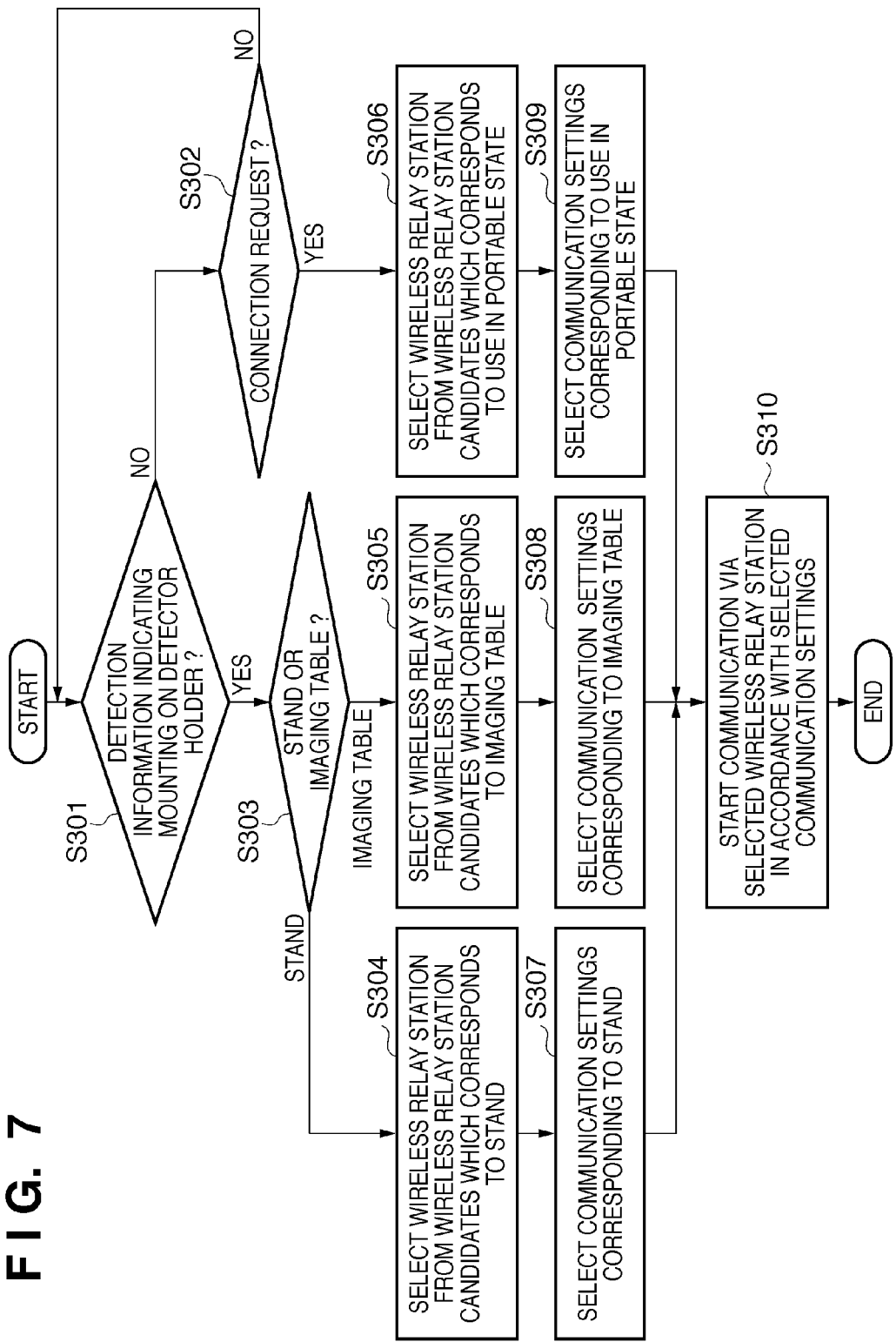
FIG. 7 is a flowchart showing an example of the operation of a control unit 4 according to the second embodiment.

An example of the operation of the control unit 4 shown in FIG. 1 will be described next with reference to FIG. 7. Operation to be performed when X-ray imaging is performed will be described below.

When capturing an X-ray image, the operator acquires an imaging order from information from an RIS (Radiology Information Systems) or the like, and mounts the electronic cassette 1 on the corresponding detector holder in accordance with the corresponding imaging technique. One of mounting detection units 16 and 26 then detects the mounting of the electronic cassette 1 on the detector holder, and sends corresponding detection information to the control unit 4.

Upon receiving the detection information, the control unit 4 causes a determination unit 81 to determine the detector holder on which the electronic cassette 1 is mounted (step S303 after YES in step S301). If the determination result indicates that the detector holder on which the electronic cassette 1 is mounted is the stand 10 ("stand" in step S303), the control unit 4 causes the relay station selection unit 82 to select relay station candidates (the wireless relay stations 62 and 63) corresponding to the stand 10. The relay station selection unit 82 selects candidates by referring to communication setting information. The relay station selection unit 82 selects one of the wireless relay stations which exhibits the optimal performance by scanning the communication levels of the relay station candidates (S304). At this time, the control unit 4 also causes a communication setting unit 84 to select communication settings corresponding to the stand 10 (S307).

If the detector holder on which the electronic cassette 1 is mounted is an imaging table 20 ("imaging table" in step S303), the control unit 4 causes the relay station selection unit 82 to select relay station candidates (wireless relay stations 64 and 65) corresponding to the imaging table 20. The relay station selection unit 82 selects candidates by referring to communication setting information. The relay station selection unit 82 then selects any one of the wireless relay stations which exhibits the optimal performance by scanning the communication levels of the relay station candidates (S305). In this case, the control unit 4 also causes the communication setting unit 84 to select communication settings corresponding to the imaging table 20 (S308).

Upon receiving a wireless communication request without receiving any detection information (YES in step S302 after NO in step S301), the control unit 4 causes the relay station selection unit 82 to select relay station candidates (wireless relay stations 64 to 67) corresponding to the use of the electronic cassette in a portable state. The relay station selection unit 82 selects any one of the wireless relay stations which exhibits the optimal performance by scanning the communication levels of the relay station candidates (S306). In this case, the control unit 4 also causes the communication setting unit 84 to select communication settings corresponding to the use of the electronic cassette in a portable state (S309).

Upon selecting a relay station and communication settings in this manner, the control unit 4 starts to communicate with the electronic cassette 1 via the selected relay station in accordance with the selected communication settings (S310).

As described above, the third embodiment is configured to perform communication upon selecting one of a plurality of relay stations provided outside detector holders. This may suppress an increase in the number of relay stations in addition to having the effects of the first embodiment.

Although the above description represents typical examples of the embodiments of the present invention, the present invention is not limited to the embodiments described above with reference to the accompanying drawings. The present invention can be modified and embodied as needed within the scope of the invention. For example, the first to third embodiments described above may be combined and executed.

Although the stand 10 and the imaging table 20 have been described as examples of detector holders in the first to third embodiments, the detector holders to be used are not limited to them. For example, it is possible to use a universal detector holder and the like. In addition, it is possible to use a plurality of the same type of detector holders (for example, two stands 10).

Although the first to third embodiments have exemplified the cases in which there are a plurality of detector holders such as the stand 10 and the imaging table 20, a single detector holder may be used. In this case, upon detecting detection information sent when the electronic cassette is mounted on the detector holder, the control unit 4 selects a wireless relay station corresponding to the detector holder. Upon receiving a wireless communication request without receiving any detection information, the control unit 4 selects a wireless relay station corresponding to the use of the electronic cassette in a portable state. The electronic cassette determines that it is mounted on a detector holder, based on the pressing of the switch 41, and selects a wireless relay station corresponding to the detector holder. Upon receiving a notification of the start of wireless communication from the wireless communication circuit 8 while no switch 41 is pressed, the electronic cassette selects a wireless relay station corresponding to the use of the electronic cassette in a portable state. The electronic cassette then sets communication settings corresponding to the selected wireless relay station, and performs communication via the selected wireless relay station. Furthermore, this system may be configured to use a plurality of detector holders without allowing the use of the electronic cassette in a portable state. In this case, the system does not perform the processing in steps S102 and S106 in FIG. 3, in steps S202 and S206 in FIG. 5, and steps S302, S306, and S309 in FIG. 7.

Note that the present invention can be embodied in the forms of, for example, a system, apparatus, method, program, and storage medium. More specifically, the present invention may be applied to a system constituted by a plurality of devices or an apparatus comprising a single device.

As has been described above, according to the above embodiments, it is possible to determine the usage pattern of the electronic cassette (radiation detector) or the mounting of the electronic cassette on a detector holder and allow the radiation detector to select a relay station for wireless communication based on the determination result. That is, when the electronic cassette is to be used in a portable state, it is possible to select a relay station provided for the use of the electronic cassette in a portable state. Performing communication using the selected relay station can implement good wireless communication. If the electronic cassette is mounted on a detector holder, it is possible to select a relay station provided for the detector holder on which the electronic cassette is mounted. Performing communication using the selected relay station can implement good wireless communication.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-256546 filed on Nov. 9, 2009, which is hereby incorporated by reference herein in its entirety.

What is claimed is:

1. A radiation imaging system comprising:
a radiation detector configured to detect radiation transmitted through an object while being in one of a portable state and a mounted state on a detector holder;
a control unit configured to control capturing of a radiographic image using said radiation detector; and
a plurality of relay stations configured to relay wireless communication from said radiation detector,
the detector holder comprising a detection unit configured to detect mounting of said radiation detector, and
said control unit comprising:
a determination unit configured to determine one of a usage pattern of said radiation detector and mounting of said radiation detector on a detector holder based on one of detection information from said detection unit and a connection request from said radiation detector, and
a selection unit configured to select one of the relay stations based on a determination result by said determination unit.

2. The system according to claim 1, wherein if said determination unit determines the mounting of said radiation detector, said selection unit selects a relay station provided inside the detector holder on which said radiation detector is mounted.

3. The system according to claim 1, wherein if said determination unit determines that said radiation detector is used in a portable state, said selection unit selects a relay station provided outside the detector holder.

4. The system according to claim 1, wherein said control unit further comprises
a storage unit configured to store setting information associating one of a usage pattern of said radiation detector and a detector holder on which said radiation detector is mounted, relay station candidates, and communication settings, and
a communication setting unit configured to perform communication setting based on the setting information stored by said storage unit,
said selection unit decides the candidate relay stations based on a determination result by said determination unit and setting information stored by said storage unit, and selects one of the relay stations based on communication intensity between each the candidate relay stations and said radiation detector, and
said communication setting unit sets a communication setting corresponding to the relay station selected by said selection unit.

5. The system according to claim 1, wherein said radiation detector comprises
a radiation detector side determination unit configured to determine one of a usage pattern of said radiation detector and mounting of said radiation detector on a detector holder, and
a radiation detector side relay station selection unit configured to select one of the relay stations based on a determination result by said radiation detector side determination unit.

6. The system according to claim 5, wherein said radiation detector comprises
a radiation detector side storage unit configured to store setting information associating one of a usage pattern of said radiation detector and a detector holder on which said radiation detector is mounted, a relay station, and a communication setting, and
a radiation detector side communication setting unit configured to perform communication setting corresponding to a relay station selected by said radiation detector side relay station selection unit based on the setting information stored by said radiation detector side storage unit.

7. The system according to claim 5, wherein housing units provided in the detector holders to mount said radiation detector include protrusions respectively having different shapes,
said radiation detector includes a plurality of switches to be pressed by a corresponding one of the protrusions when said radiation detector is housed in said housing unit, and
said radiation detector side determination unit determines one of a usage pattern of said radiation detector and a detector holder on which said radiation detector is mounted, based on a pressed state of one of the switches.

8. A control apparatus which controls capturing of a radiographic image using a radiation detector configured to detect radiation transmitted through an object while being in a portable state or mounted on a detector holder, said apparatus comprising:

a determination unit configured to determine one of a usage pattern of said radiation detector and mounting of said radiation detector on a detector holder based on one of information from the detector holder and a connection request from said radiation detector; and a selection unit configured to select a relay station, from a plurality of relay stations, which relays wireless communication from said radiation detector, based on a determination result by said determination unit.

9. A radiation detector which detects radiation transmitted through an object while being in one of a portable state and a mounted state on a detector holder, said detector comprising:

a determination unit configured to determine one of a usage pattern of the radiation detector and mounting of the radiation detector on a detector holder; and a selection unit configured to select a relay station, from a plurality of relay stations, based on a determination result by said determination unit.

10. The detector according to claim 9, further comprising a setting unit configured to set a communication setting corresponding to a relay station selected by said selection unit.

11. The detector according to claim 9, wherein if said determination unit determines the mounting of said detector holder, said selection unit selects a relay station corresponding to the detector holder on which said radiation detector is mounted.

12. The detector according to claim 9, wherein if said determination unit determines that the radiation detector is used in a portable state, said selection unit selects a relay station provided for use of the radiation detector in a portable state.

13. A relay station selection method in a radiation imaging system comprising a radiation detector configured to detect radiation transmitted through an object while being in one of a portable state and a mounted state on a detector holder, a control unit configured to control capturing of a radiographic image using the radiation detector, and a plurality of relay stations configured to relay wireless communication from the radiation detector, the method comprising:

determining one of a usage pattern of the radiation detector and mounting of the radiation detector on a detector holder based on one of detection information indicating mounting of the radiation detector and a connection request from the radiation detector; and selecting one of the relay stations based on the determination result, and selecting one of the relay stations based on the determination result.

14. A control apparatus in a radiation imaging system which communicates wirelessly a radiographic image detected by a radiation detector via a relay station, comprising:

a determination unit configured to determine a usage pattern of the radiation detector, and a selection unit configured to select the relay station for using the wireless communication, based on a determination result by the determination unit.

15. The apparatus according to claim 14, wherein the determination unit determines the usage pattern based on installation of the radiation detector on a detector holder.

16. The apparatus according to claim 14, wherein the determination unit determines the usage pattern based on information transmitted by the radiation detector.

17. The apparatus according to claim 14, wherein the determination unit determines the usage pattern based on information transmitted by a detector holder which installed the radiation detector.

18. The apparatus according to claim 14, wherein the determination unit determines that the usage pattern is a portable usage.

19. The apparatus according to claim 14, wherein the determination unit determines that the usage pattern is a usage of the radiation detector installed on a detector holder.

20. The apparatus according to claim 14, further comprising:

a communication unit configured to communicate with the radiation detector via the selected relay station, based on a communication setting corresponding to the selected relay station.

21. A control apparatus in a radiation imaging system which communicates a radiographic image captured by a radiation detector via a relay station, comprising:

a detecting unit configured to detect installation of the radiation detector on a detector holder, and a selection unit configured to select the relay station for using the wireless communication, based on the detector holder on which is installed the radiation detector.

22. The apparatus according to claim 21, wherein the detecting unit detects the installation of radiation detector, based on a signal transmitted by the radiation detector.

23. The apparatus according to claim 21, wherein the detecting unit detects the installation of radiation detector, based on a signal transmitted by the detector holder which installed the radiation detector.

24. The apparatus according to claim 21, further comprising:

a communication unit configured to communicate with the radiation detector via the selected relay station, based on a communication setting corresponding to the selected relay station.

25. A radiation detector which communicates a detected radiographic image via a relay station, comprising:

a detect unit configured to detect a usage pattern of the radiation detector, and a selection unit configured to select the relay station based on a detection result by said detect unit.

26. The detector according to claim 25, wherein the detect unit detects the usage pattern based on a detector holder installed in the radiation detector.

27. The detector according to claim 25, further comprising a setting unit configured to set a communication setting corresponding to the selected relay station.

28. The detector according to claim 25, wherein the selection unit selects the relay station corresponding to a detector holder which is installed in the radiation detector.

29. The detector according to claim 25, wherein if the usage pattern is a portable usage, the selection unit selects a relay station provided for use of the radiation detector in the portable usage.

30. The detector according to claim 25, wherein if the usage pattern is a usage of the radiation detector installed on a detector holder, the selection unit selects a relay station provided for use of the radiation detector in the usage.

31. A radiation detector which communicates a detected radiographic image via a relay station, comprising:

a detect unit configured to detect installation of the radiation detector on a detector holder, and a selection unit configured to select the relay station based on the detector holder on which is installed the radiation detector.

32. The detector according to claim 31, further comprising a setting unit configured to set a communication setting corresponding to the selected relay station.

33. The detector according to claim 31, wherein the selection unit selects the relay station corresponding to the detector holder on which the radiation detector is installed.

34. A control method for a radiation imaging system which communicates wirelessly a radiographic image detected by a radiation detector via a relay station, the method comprising:
   determining a usage pattern of the radiation detector, and
   selecting the relay station for using the wireless communication, based on a result of the determining.

35. A control method for a radiation imaging system which communicates a radiographic image captured by a radiation detector via a relay station, the method comprising:
   detecting installation of the radiation detector on a detector holder, and
   selecting the relay station for using wireless communication, based on the detector holder on which is installed the radiation detector.

36. A method for a radiation detector which communicates a detected radiographic image via a relay station, the method comprising:
   detecting a usage pattern of the radiation detector, and
   selecting the relay station based on a result of the detecting.

37. A method for a radiation detector which communicates a detected radiographic image via a relay station, the method comprising:
   detecting installation of the radiation detector on a detector holder, and
   selecting the relay station based on the detector holder on which is installed the radiation detector.

38. A non-transitory computer-readable medium storing a computer program having instructions which, when executed by a computer, perform a method for a radiation imaging system which communicates wirelessly a radiographic image detected by a radiation detector via a relay station, the method comprising:
   determining a usage pattern of the radiation detector, and
   selecting the relay station for using wireless communication, based on a determination result by the determining.

39. A non-transitory computer-readable medium storing a computer program having instructions which, when executed by a computer, perform a method for a radiation imaging system which communicates a radiographic image captured by a radiation detector via a relay station, the method comprising:
   detecting installation of the radiation detector on a detector holder, and
   selecting the relay station for using wireless communication, based on the detector holder on which the radiation detector is installed.

40. A non-transitory computer-readable medium storing a computer program having instructions which, when executed by a computer, perform a method for a radiation detector which communicates a detected radiographic image via a relay station, the method comprising:
   detecting a usage pattern of the radiation detector, and
   selecting the relay station based on a result of the detecting.

41. A non-transitory computer-readable medium storing a computer program having instructions which, when executed by a computer, perform a method for a radiation imaging system which communicates a radiographic image captured by a radiation detector via a relay station, the method comprising:
   detecting installation of the radiation detector on a detector holder, and
   selecting the relay station for using communication, based on the detector holder on which is installed the radiation detector.

* * * * *